United States Patent [19]

La Londe et al.

[11] 4,011,327
[45] Mar. 8, 1977

[54] COMPOSITIONS CONTAINING 7β-ALKYLTHIODEOXYNUPHARADIN-6α-OLS

[75] Inventors: Robert Thomas La Londe; Amy Inn-Mei Tsai, both of Syracuse; Chun Juan Wang, Jamesville; Chunfook Wong, Syracuse, all of N.Y.

[73] Assignee: Research Corporation, New York, N.Y.

[22] Filed: Jan. 31, 1975

[21] Appl. No.: 546,191

[52] U.S. Cl. .................................. 424/256; 424/16
[51] Int. Cl.$^2$ ...................... A01N 9/00; A01N 9/22
[58] Field of Search .................................. 424/256

[56] References Cited

OTHER PUBLICATIONS

Cullen et al., 1973, vol. 79, p. 100921a, Chem. Abs.
LaLonde et al., Chem. Abs., 1971, vol. 75, p. 20724r.
Achmatowicz et al., Chem. Abs., 1964, vol. 61, p. 3157c.
Chem. Abs., 1963, vol. 59, p. 3973.
Arata et al., Chem. Abs., vol. 53, pp. 10215, 10216.
Arata, Chem. Abs., vol. 51, p. 6637, 1957.

*Primary Examiner*—Dale R. Ore
*Attorney, Agent, or Firm*—Cooper, Dunham, Clark, Griffin & Moran

[57] ABSTRACT

Pharmaceutical compositions containing 7-alkylthiodeoxynupharidin-6-ols or 7-alkylthioalkylenedeoxynupharidin-6-ols are useful in the control of fungus infections.

8 Claims, No Drawings

COMPOSITIONS CONTAINING 7β-ALKYLTHIODEOXYNUPHARADIN-6α-OLS

The invention described herein was made in the course of work under a grant or award from the Department of Health, Education and Welfare.

This invention is concerned with novel therapeutic compositions and their use. More particularly, it is concerned with compositions containing certain 7-substituted deoxynupharidines which are useful to inhibit the growth of pathogenic microorganisms and in the control of mammalian diseases.

The compound nupharidine is a naturally occurring N-oxide which can be isolated from the rhizomes of Nuphar luteum. It can be converted to 6-dehydrodeoxynupharidine through Polonovski type eliminations with acetic anhydride or trifluoroacetic anhydride as described in the Journal of the American Chemical Society 93, 2501 (1971). The dehydro compound, on treatment with selected thiosulfonates is converted to a mixture of 7α or 7β substituted thiodeoxynupharidines, the preferred compounds of the invention. These compounds are antimicrobial agents, particularly active against pathogenic fungi. Mixtures of the isomers can be employed, or the isomers can be separated for use. The 7β-compounds appear to be somewhat more stable.

The above identified article describes the preparation of 6-dehydrodeoxynupharidine as follows: "(−)-Δ$^6$-Dehydrodeoxynupharidine Using $(CF_3CO_2)_2O$. A solution of 1 g of nupharidine (4 mmol) in 15 ml of dry methylene chloride was cooled to 0° and treated with 890 mg of trifluoroacetic anhydride (4.2 mmol) at 0° for 2 hr and at 25° for 80 hr under nitrogen. The methylene chloride was evaporated and the residue was basified with 10% methanolic potassium hydroxide. The methanol was evaporated and the residue triturated with ether. The ether solution was washed with water then dried $(Na_2SO_4)$. Evaporation of the combined water wash solution afforded 396 mg of unconverted nupharidine. "Evaporation of the ether gave 390 mg of crude Δ$^6$-enamine identified by ir and nmr."

The substituted thioalkylenedeoxynupharidines within the scope of the invention are prepared by treatment of 6-dehydrodeoxynupharidine with a haloalkyl alkyl sulfide such as 2-bromoethyl ethyl sulfide or 2-bromoethyl benzyl sulfide.

While a number of 7α- and 7β-substituted thio- and substituted thioalkylenedeoxynupharidines have useful anti-microbial activity in the compositions of this invention, the presently preferred compounds, which are preferred because they are relatively easy to produce and therefore economical, are those represented by the formulas:

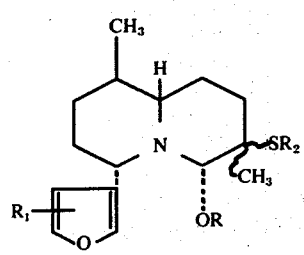

-continued

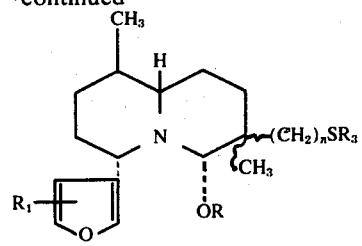

wherein:
  n is an integer from 0 to 2;
  R is hydrogen, alkyl containing up to eight carbon atoms, or acyl containing up to eight carbon atoms;
  $R_1$ is hydrogen, alkyl containing up to about 3 carbon atoms, aralkyl containing up to 10 carbon atoms in the aryl group and up to 3 carbon atoms in the alkyl group, carboxy, carbalkoxy containing up to 4 carbon atoms, amino, amido, hydroxy, alkoxy containing up to 4 carbon atoms, keto containing up to 4 carbon atoms, aldehydo, halo, nitro, nitrilo, mercapto, thioalkoxy containing up to 4 carbon atoms and heterocyclic moieties;
  $R_2$ is alkyl, cyclic alkyl, alkylene, cyclic alkylene, alkylyne and cyclic alkylyne containing up to 6 carbon atoms including substituted analogs thereof in which a substituent is halogen, amino, alkylamino, dialkylamino, phenylamino, diphenylamino, alkylphenylamino, hydroxyl, acylated hydroxyl, carboxy, or carbalkoxy, an alkyl or acyl group containing up to 6 carbon atoms and up to eight carbon atoms respectively;
  $R_3$ is alkyl containing up to 5 carbon atoms or aralkyl containing up to 2 carbon atoms in the alkyl group and 10 carbon atoms in the aryl group.

The invention also includes ammonium, metallic and acid addition salts of the above identified compounds within its scope.

The substituted thio compounds which are useful in this invention are readily prepared by reaction between 6-dehydrodeoxynupharidine and an appropriately substituted thiosulfonate such as benzenethiosulfonate, or 2-butenyl methanethiosulfonate.

Typical compounds within the scope of the invention include:

7β-methylthiodeoxynupharidin-6α-ol
  7β-isobutylthiodeoxynupharidin-6α-ol 6-acetate
  7β-cyclopropylthiodeoxynupharidin-6α-ol
  7β-cyclohexadienylthiodeoxynupharidin-6α-ol
  6-propoxyl-7β-(2-diphenylamino) propylthiodeoxynupharidine
  7β-(3-dimethylamino-4-carbomethoxy) butylthiodeoxynupharidin-6α-ol
  7β-(2-chloro) butylthiodeoxynupharidin-6α-ol
  7β-(2-hexenyl) thiodeoxynupharidin-6α-ol
  7β-(1,3-butadienyl) thiodeoxynupharidin-6α-ol
  7β-(1-propynyl) thiodeoxynupharidin-6α-ol
  7β-(2-hexynyl) thiodeoxynupharidin-6α-ol 6-hexanoate All of the compounds necessary to prepare compounds such as above are known or can be prepared by known reactions; for example, by reaction of an appropriate thiol with sulfuryl chloride, or by reaction of potassium or sodium methane, benzene or toluenethiosulfonate with an appropriate alkyl, alkenyl or alkynyl alkylating agent.

The 7-alkylthioalkylenedeoxynupharidines or the corresponding aralkyl compounds of this invention are prepared by reaction between a haloalkyl alkyl or aralkyl sulfide and 6-dehydrodeoxynupharidine in a reaction inert, anhydrous, organic solvent in the presence of an alkaline reagent at an elevated temperature for from 2 to 6 hours.

Suitable solvents include liquid aromatic hydrocarbons containing up to 10 carbon atoms such as benzene, toluene or xylene. Alkaline reagents which are especially useful include alkali metal carbonates and bicarbonates, particularly sodium or potassium bicarbonate. The reaction temperature is normally from about 70° C to 100° C.

It is best to carry out the reaction in an inert atmosphere, suitably a nitrogen atmosphere.

As stated above, the scope of the invention includes compounds in which the furyl ring is substituted. Such compounds are prepared from deoxynupharidine by the sequence of reactions which include:
1. Substitution on the furyl ring
2. Oxidation to an N-oxide
3. Polonovski elimination
4. Conversion to final products by the reactions described above The furyl ring of deoxynupharidine can be acylated or nitrated by the procedure of Arata and Yamonouche as described in Yakugaku Zasshi, 91, 476 (1971). The acylated compound may be converted to an alkyl compound by a Wolff-Kishner reduction, or to a carboxy substituted compound by oxidation. The latter compound can be readily esterified by the usual esterification techniques. Amino substituted compounds are produced by reduction of nitro compounds.

The preparation of certain compounds within the scope of this invention require that precautions be taken to protect active hydrogen containing substituents such as carboxy, amino, or hydroxy substituents. The first mentioned group is readily protected by conversion to an ester. Amino and hydroxyl groups can be protected by acylation. The protective groups selected should be ones that are easily removed.

As will be recognized, certain of the compounds illustrated above are acidic or basic in nature. These can be readily converted to pharmaceutically acceptable ammonium, metallic or acid addition salts. It is specifically intended to include all such salts within the scope of this invention.

Typically useful metallic salts include alkali and alkaline earth metal salts of carboxy substituted compounds. Calcium, potassium and sodium salts are preferred. The preferred ammonium salts are tetraalkyl ammonium salts in which an alkyl group contains up to 4 carbon atoms. Typical examples of such compounds are calcium, potassium, sodium and tetraethyl ammonium salts of:

7$\beta$-(2-carboxyalkylene)-thiodeoxynupharidin-6$\alpha$-ol
7$\beta$-(3-carboxypropylene)-thiodeoxynupharidin-6$\alpha$-ol Typically useful acid addition salts include those derived by reaction of a pharmaceutically acceptable organic or inorganic acid with a primary, secondary or tertiary amino substituted arylthiodeoxynupharidin-ol. Such acids as hydrochloric, hydrobromic, sulfuric, nitric, phosphoric, acetic, propionic, gluconic, glutaric, tartaric, citric, maleic and succinic are mentioned by way of example. These salts may be formed by reaction between the selected acid and a substrate such as 7$\beta$-(2-aminoethyl)-thiodeoxynupharidin-6$\alpha$-ol
7$\beta$-(2-methylaminohexyl)-thiodeoxynupharidin-6$\alpha$-ol
7$\beta$-(2,3-diaminophenyl)-thiodeoxynupharidin-6$\alpha$-ol
7$\beta$-(2-dimethylaminopropyl)-thiodeoxynupharidin-6$\alpha$-ol The 7-substituted thio compounds of this invention are prepared by reaction in an inert solvent between the selected sulfonate thioester and 6-dehydrodeoxynupharidine. Typically useful organic solvents include hydrocarbon and halogenated hydrocarbon solvents, particularly aromatic hydrocarbon solvents such as benzene or toluene.

While a wide range of reaction temperatures from 0° C to 90° C of even higher can be tolerated in suitable cases, it is most advantageous and convenient to carry out the reaction at ambient temperature, say 20° C to 40° C since undesirable side reactions may take place at higher temperatures.

The reaction period will depend upon the selected temperature. In the range disclosed above, from 10 to 48 hours are normally adequate. At ambient temperatures, a time period of from 20 to 30 hours is preferred.

The reaction is best called out in the presence of a suitable adsorbent which is effective to trap the intermediate immonium ion and thereby to prevent the occurence of the reverse equilibrium reaction. The adsorbent is not essential however. A wide variety of adsorbents may be employed. These include, for example, aluminum oxide and partially hydrated aluminum oxide, as well as charcoal, powdered cellulose and magnesium silicate. The preferred adsorbent is partially hydrated aluminum oxide. Typically, the adsorbent is added in a weight range of from 2 to 10 times the weight of 6-dehydrodeoxynupharidine.

It is desirable to carry out the reaction in an inert atmosphere to limit the possibility of undesirable side reactions. An atmosphere of nitrogen is generally most convenient, although helium could also be employed.

The reaction product is a mixture of the 7$\alpha$- and the 7$\beta$- substituted compounds, for example, 7$\alpha$-methylthio-7-epideoxynupharidin-6$\beta$-ol and 7$\beta$-methylthiodeoxynupharidin-6$\alpha$-ol. These are readily separated by chemical or physical means, suitably chromotography using successively more polar solvents on an absorbent such as alumina. The $\beta$-compound normally separates first, but the effect of substituents on the aryl ring may reverse the normal separation order. It is not necessary to separate, since mixtures of the $\alpha$- and $\beta$-isomers may be employed.

The products of this invention have an inhibitory effect on the growth of a variety of microorganisms including such human pathogenic fungi as (1) *Histoplasma capsulatum*, (2) *Blastomyces dermatitidis*, (3) *Trichophyton rubrum*, and (4) *Sporotrichum schenckii*.

The minimum in vitro inhibitory concentration of 7$\beta$-methylthiodeoxynupharidin-6$\alpha$-ol against these microorganisms in mcg/ml for a two week period as well as the disease and symptomatology usually associated with a mammalian infection by the microorganism is shown in Table 1.

TABLE 1

| Micro-organism | Conc. in mcg/ml | Disease | Symptomatology |
|---|---|---|---|
| 1 | 40 | Histoplasmosis | Cough, fever, emaciation, distress and difficulty in breathing, enlargement of hilar lymph glands, low leucocyte count, nodular red skin blotches, ulceration of naso-oral pharyngeal cavities and intestines, enlargement of spleen and liver. |
| 2 | 80 | Blastomycosis | Cough, chest pains, low grade fever, distress and difficulty in breathing, lung lesions, cutaneous lesions, inflammation of lymph vessels and enlargement of lymph nodes. |
| 3 | 100 | Dermatomycosis | Dermatitis, scalp lesions, scales on pubic and scalp hair, deterioration of nails. |
| 4 | 100 | Sporotrichosis | Subcutaneous nodules and cutaneous lesions, ulceration of naso-oral pharyngeal regions occasionally associated with angina, stomatitis, glossitis, laryngitis and rhinitis. |

The compounds of this invention when used in the treatment of various diseases of man and animals will be utilized in association with a pharmaceutically acceptable carrier. The selection of a carrier will depend on a variety of well recognized factors such as the reactivity of the physiologically active compound, the condition under treatment and the chosen route of administration.

For oral administration, the pharmaceutical compositions may be provided in the form of capsules and tablets including such excipients as starch, sugars and various forms of clay. Elixirs and syrups may be provided as aqueous solutions or suspensions containing solubilizing, coloring, thickening or flavoring agents in accordance with standard practice. Parenteral dosage forms will normally be provided as isotonic solutions with physiological saline or glucose. For topical administration various pastes or oils, suitably a hydrocarbon fraction such as petroleum, may serve as the carrier. In the various dosage unit forms, the compositions may contain from about 0.25 and 10% by weight, based on the total weight of the selected nupharidine derivative as the principal active ingredient.

The toxicity of the compounds used in the compositions of the invention is low in mice. Even at a level as high as 200 mg/kg of body weight no toxic manifestations are observed with the compounds of this invention. This latter level represents a feeding to a mouse at a daily rate of 0.2% of its body weight. These results indicate that the compounds used in the compositions of this invention are substantially safe for use at all commonly employed dosage levels.

The novel compounds of this invention may be utilized as antimicrobial agents and may be administered in doses of from about 20 to 100 mg per kg of body weight per day. The physician or veterinarian in attendance will determine the optimum effective dosage and this will depend upon such factors as the age and weight of the patient, the condition under treatment including its stage of advancement, the selected route of administration and other factors well known to those skilled in the art.

The following non-limiting examples are given by way of illustration only.

EXAMPLE 1

Preparation of 7$\beta$-Methylthiodeoxynupharidin-6$\alpha$-ol and 7$\alpha$-Methylthio-7-epideoxynupharidin-6$\beta$-ol A solution of 412 mg of $\Delta^6$-dehydrodeoxynupharidine in 20 ml of anhydrous $C_6H_6$ was treated with 383 mg of methyl p-toluenethiosulfonate in the presence of 2 g of alumina (neutral, activity III) at 25° C under nitrogen overnight. The solvent was evaporated and the residue was chromatographed on a column of alumina (60 g. neutral, 5% $H_2O$) 3 cm in diameter. The column was eluted with: 120 ml of $C_6H_6$-hexane, 1:9 (fraction 1); 70 ml of $C_6H_6$ (fraction 2); 200 ml of $C_6H_6$ (fraction 3); 100 ml of $C_6H_6$ (fraction 4); 200 ml of $C_6H_6$-ether, 9:1 (fraction 5). Fraction 4 was pure 7$\beta$-methylthiodeoxynupharidin-6$\alpha$-ol: uv $\epsilon_{210}$ $C_2H_5OH$ end absorption $\lambda_{max}$ $C_2H_5OH(H+)$ 294 nm ($\epsilon$ 2460) ir ($CCl_4$) 2.85 (s, br: H bonded OH), 11.5 $\mu$ (3-furyl), Bohlmann bands absent; nmr ($CDCl_3$) $\delta$ 0.90 (d, J = 4 Hz, 3 H, C-1 $CH_3$), 1.38 (s, 3 H, C-7 $CH_3$), 1.85 (s, 3H, $CH_3S$), 2.88 (d, J – 1 Hz, 1 H, OH, exchanged by addition of $D_2O$), 3,76 (m, 1 H, C-4 H), 4.15 (d, J = 1 Hz, 1 H, C–6 H), 6.4 (m, 1 H, $\beta$H of 3-furyl), 7.4 (m, 2H, $\alpha$H of 3-furyl); nmr ($C_6H_6$) $\delta$ 0.82 (d, J = 4 Hz, 3 H, C-1 $CH_3$), 1.35 (s, 3 H, C-7 $CH_3$), 1.52 (s, 3 H, $CH_3S$), 2.98 (d, J = 1.5 Hz, 1 H, OH, exchanged by addition of $D_2O$), 3.90 (m, 1 H, C-4 H), 4.27 (br s and sharpening after D exchange at OH, 1 H, C-6 H), ms m/e (rel. intensity) 295 (100) (M+), 280 (13.5), 278 (31), 266 (50), 248 (84), 231 (41.5), 218 (39.5), 192 (47), 175 (13), 176 (13.5), 164 (22.5), 136 (18), 107 (91, 94 (70), 81 (46).

Fraction 6 (200 ml of 1:9 ether-benzene) was pure 7$\alpha$-methylthio-7-epideoxy-nupharidin-6$\beta$-ol: mp 79°–80°; uv $\epsilon_{210}$ $C_2H_5OH$ end absorption, $\lambda_{max}$ ($C_2H_5OH$, H+) 295 ($\epsilon$ 1610); ir ($CCl_4$) 2.75 (s, sharp, free OH), 2,86 (s, br, H bonded OH), 11.46 $\mu$ (3-furyl), Bohlmann bands absent; nmr $\delta$ 0.95 (d, J = 4.5 Hz, 3 H, C-1 $CH_3$), 1.23 (br s, 3H, C-7 $CH_3$), 1.87 (s, 3H, CH$_3$S), 4.23 (br s, 1 H, C-6 H), 6.5 (m, 1 H, βH of 3-furyl), 7.37 (m, 2 H, αH of 3-furyl); nmr (C$_6$H$_6$) δ 0.84 (d, J = 4 Hz, 3 H, C-1 CH$_3$), 1.13 (s, 3 H, C-7 CH$_3$), 1.70 (s, 3H, CH$_3$S), 3.55 (m, 1 H, C-4 H), 4.5 (d, J = 4.5 Hz and s after D exchange at OH, 1 H, C-6-H); ms m/e (rel. intensity) 323 (7), 308 (4), 295 (74) (M$^+$), 280 (13), 278 (23), 277 (38), 264 (36), 248 (66), 231 (78), 216 (39), 192 (34.5), 176 (29), 164 (44), 136 (19), 107 (100), 94 (87), 81 (52).

EXAMPLE 2

Immonium Perchlorate Salt from 7β-Methylthiodeoxynupharidin-6α-ol

An 84 mg. sample of fraction 4 from Example 1 was treated with 0.2 M aqueous HClO$_4$ (1 equiv.) and sufficient C$_2$H$_5$OH for homogeneity was added. The solvent was evaporated at 40° C to obtain 35 mg. of crystalline immonium perchlorate salt: mp 179°–180° C; ir (KBr) 6.02 μ.

Anal. Calcd. for C$_{16}$H$_{24}$NO$_5$SCl: C, 50.90; H, 6.40; N, 3,71; S, 8.49. Found: C. 50.92; H, 6.43; N, 3.85; S, 8.69.

EXAMPLE 3

6α-Acetoxy-7β-methylthiodeoxynupharidine

To a dioxane solution (1.0 ml) containing 30 mg of 7β-methylthiodeoxynupharidin-6α-ol is added 6.1 mg of glacial acetic acid at ambient temperature. Thereafter the dioxane is removed by vacuum evaporation to obtain a mixture of 6α-acetoxy-7β-methylthiodeoxynupharidine and the immonium acetate salt from 7β-methylthiodeoxynupharidin-6α-ol.

EXAMPLE 4

6α-Methoxy-7β-methylthiodeoxynupharidine

A severalfold excess of anhydrous methanol is added to 11 mg of 7β-methylthiodeoxynupharidin-6α-ol and the methanol is removed by vacuum evaporation. The addition of methanol and vacuum evaporation is repeated several times. The residue consists of 6α-methoxy-7β-methylthiodeoxynupharidine.

EXAMPLE 5

6α-Isobutoxy-7β-butylthiodeoxynupharidine

A severalfold excess of anhydrous isobutyl alcohol is added to 20 mg. of 7β-butylthiodeoxynupharidin-6α-ol and the isobutyl alcohol is removed by vacuum evaporation. The addition of isobutyl alcohol and vacuum evaporation is repeated several times. The residue consists of 6α-isobutoxy-7β-butylthiodeoxynupharidine.

EXAMPLE 6

7α-Butylthiodeoxynupharidin-6β-ol and 7β-Butylthiodeoxynupharidin-6α-ol

Carbontetrachloride solution (60 ml) of 230 mg. of 6-dehydrodeoxynupharidine, 252 mg. of n-butyl p-toluenethiosulfonate and 1.2 g. of suspended neutral aluminum oxide (activity 2) is stored in the dark, at 25° C under nitrogen for 14 hours. The reaction mixture then is processed and separated as in Example 1 and thereby the separate title compounds are obtained.

EXAMPLE 7

7α-(2-Propyl)-thiodeoxynupharidin-6β-ol and 7β-(2-Propyl)-thiodeoxynupharidin-6α-ol An anhydrous toluene solution (60 ml) containing 450 mg of 6-dehydrodeoxynupharidine, 490 mg of isopropyl p-toluenethiosulfonate and 3.5 g of suspended neutral aluminum oxide (activity 4) is stored in the dark under nitrogen at 25° C for 24 hours. Thereafter the reaction mixture is processed and separated as in Example 1 to obtain the separate title compounds.

EXAMPLE 8

7α-Crotylthiodeoxynupharidin-6β-ol and 7β-Crotylthiodeoxynupharidin-6α-ol

An anhydrous benzene solution (150 ml) containing 680 mg of 6-dehydrodeoxynupharidine, 750 mg of crotyl p-toluenethiosulfonate and 2.8 g of suspended neutral aluminum oxide (activity 3) is stored in the dark under argon at 25° C for 30 hours. Thereafter the reaction mixture is processed and separated as in Example 1 to obtain the separate title compounds.

EXAMPLE 9

7α-(3-pentynyl)-thiodeoxynupharidin-6β-ol and 7β-(3-pentynyl)-thiodeoxynupharidin-6α-ol A benzene solution (50 ml) containing 250 ml of 6-dehydrodeoxynupharidine, 283 mg of 3-pentynyl benzenethiosulfonate and 750 mg of suspended neutral aluminum oxide (activity 2) is stored in the dark under nitrogen at 15° C for 24 hours. Thereafter the reaction mixture is processed and separated as in Example 1 to obtain the separate title compounds.

EXAMPLE 10

7α-Cyclohexylthiodeoxynupharidin-6β-ol and 7β-Cyclohexylthiodeoxynupharidin-6α-ol A flask containing 231 mg of cyclohexyl cyclohexanethiosulfonate, 290 mg of 6-dehydrodeoxynupharidine and 400 mg of powdered charcoal is repeatedly vacuum evacuated and purged with helium. A 60 ml quantity of xylene is distilled under helium into the reaction flask and the resulting mixture is stirred rapidly and warmed to 80° C under helium. After 10 hours at 80° C the flask is cooled and its contents are processed and separated as in Example 1.

EXAMPLE 11

7α-Carbo-t-butoxymethylthiodeoxynupharidin-6β-ol and 7β-Carbo-t-butoxymethylthiodeoxynupharidin-6α-ol An anhydrous benzene solution (90 ml) containing 470 mg of 6-dehydrodeoxynupharidin, 620 mg of carbo-t-butoxymethyl toluenethiosulfonate and 950 mg of freshly deadsorbed powdered cellulose, stirred to suspension is stored in the dark under nitrogen at 25° C for 20 hours. Thereafter the reaction mixture is processed and separated as in Example 1 to obtain the separate title compounds.

EXAMPLE 12

7α-[2-(N-methyl-N-phenylamino)-ethyl]-thiodeoxynupharidin-6β-ol and
7β-[2-(N-methyl-N-phenylamino)-ethyl]-thiodeoxynupharidin-6α-ol A benzene solution (28 ml) containing 230 mg of 6-dehydrodeoxynupharidine, 320 mg of 2-(N-methyl-N-phenylamino)-ethyl methanethiosulfonate and 1.5 g of suspended powdered aluminum oxide is stored in the dark under nitrogen at 15° C for 18 hours. Threafter the reaction mixture is processed and separated as in Example 1 to obtain the separate title compounds.

EXAMPLE 13

The Immonium-ammonium Dichloride from 7β-[2-(N-methyl-N-phenylamino)-ethyl]-thiodeoxynupharidin-6α-ol A dioxane-water solution of 7β-[2-(N-methyl-N-phenylamino)-ethyl]-thiodeoxynupharidine-6α-ol is treated with a 5% excess of hydrochloric acid. Thereafter the vessel is warmed slightly and vacuum evacuated to obtain the immonium-ammonium dichloride.

EXAMPLE 14

The Immonium-chloride Salt from 7β-Carboxymethylthiodeoxynupharidin-6α-ol

A dioxane-water solution of 7β-carbo-t-butoxymethylthiodeoxynupharidin-6α-ol (Example 10) was warmed with slightly more than twice an equal molar amount of hydrochloric acid. Thereafter the solvent is vacuum evaporated to obtain the title compound.

EXAMPLE 15

The Sodium Salt from 7β-Carboxy-methylthiodeoxynupharidin-6α-ol

The immonium chloride salt from 7β-carboxymethylthiodeoxynupharidin-6α-ol (Example 14) in dioxane water is treated with twice an equal molar amount of sodium hydroxide. Thereafter the solvent is removed by vacuum evaporation.

EXAMPLE 16

7α-Methylthiomethylene-7-epideoxynupharidin-6β-ol and 7β-Methylthiothylenedeoxynupharidin-6α-ol An anhydrous benzene solution (90 ml) containing 600 mg of 6-dehydrodeoxynupharidine and a 20% molar excess of 2-bromomethyl methyl sulfide together with 0.5 g of solid sodium bicarbonate is maintained at 80° C to 90° C for 4 hours under nitrogen. An equal volume of ether is added, and the mixture is shaken with 50 ml of 5% aqueous potassium hydroxide solution. The organic layer is separated, dried over anhydrous sodium sulfate, filtered and evaporated to dryness. The mixture is then processed and separated as in Example 1.

EXAMPLE 17

Antifungal Activity

Preparation of a solution of 7 -MTDOL suitable for running the antifungal tests was carried out in the following manner.

A 50 mg sample of 7-MTDOL was dissolved in a mixture of 30 mg of acetic acid and 1 ml of dimethylsulfoxide. The resulting solution was then employed to inhibit the growth of the microorganisms in vitro. The solvent blank which was used for comparison purposes was made up in a similar manner. Thus 60 mg of acetic and 2 ml of dimethylsulfoxide was diluted to 100 ml with water. These solutions of 7-MTDOL and reference solvent were sterilized by filtering through a Seitz filter.

The mycelial growth of *Blastomyces dermatitidis* and *Histoplasma capsulatum* was inhibited up to the end of 3 weeks by concentrations of 80 and 40 μg /ml respectively of 7-MTDOL in Sabouraud dextrose agar. The sensitivity of these two fungi to 7-MTDOL is shown in Table 2. The growth of *Trichophyton rubrum* and *Sporotrichum schenckii* was inhibited up to the end of 3 weeks by concentrations of 100 μg /ml of 7-MTDOL in Sabouraud dextrose agar. These results are also given in Table 2.

TABLE 2

Sensitivities of *Histoplasma*, *Blastomyces*, *Trichophyton* and *Sporotrichum* to 7-MTDOL as Expressed by Weekly Increments of the Diameter of Colony (in mm) on Sabouraud Dextrose Agar at 25° C (Mycelial phase)

TABLE 2

| Concentration of Alkaloid mcg/ml | | *Histoplasma capsulatum* No. 1106 Week | | | *Blastomyces dermatitidis* No. 1107 Week | | | *Trichophyton rubrum* No. 1112 Week | | | *Sporotrichum schenckii* No. 1109 Week | | |
|---|---|---|---|---|---|---|---|---|---|---|---|---|---|
| | | 1 | 2 | 3 | 1 | 2 | 3 | 1 | 2 | 3 | 1 | 2 | 3 |
| 100 | a | 0 | 0 | 0 | 0 | 0 | T | T | 5 | 6 | 0 | 0 | * |
| | b | 0 | 0 | 0 | 0 | T | 5 | 0 | T | 7 | 0 | 0 | 0 |
| 80 | a | 0 | 0 | 0 | 0 | 0 | 0 | 0 | 5 | 9 | 0 | 0 | T |
| | b | 0 | 0 | 0 | 0 | 0 | T | 0 | 5 | 6 | 0 | 0 | 6 |
| 60 | a | 0 | 0 | * | 0 | 5 | 5 | 0 | 8 | 14 | 0 | * | * |
| | b | 0 | 0 | 0 | 0 | 5 | 7 | 6 | 6 | 15 | 0 | 10 | 20 |
| 40 | a | 0 | T | T | 7 | 15 | 20 | 8 | 20 | 30 | T | 18* | 18* |
| | b | 0 | 0 | 0 | 6 | 15 | 28 | 6 | 18 | 26 | T | 15 | 25 |
| | a | 0 | T | 10 | 10 | 16 | 17 | 8 | 21 | 30 | T | 20 | 31 |

TABLE 2-continued

Sensitivities of *Histoplasma*, *Blastomyces*, *Trichophyton* and *Sporotrichum* to 7-MTDOL as Expressed by Weekly Increments of the Diameter of Colony (in mm) on Sabouraud Dextrose Agar at 25° C (Mycelial phase)

| Concentration of Alkaloid mcg/ml | | Histoplasma capsulatum No. 1106 Week | | | Blastomyces dermatitidis No. 1107 Week | | | Trichophyton rubrum No. 1112